United States Patent [19]

Inaba et al.

[11] 3,950,526
[45] Apr. 13, 1976

[54] QUINAZOLINE DERIVATIVES IN PHARMACEUTICAL COMPOSITIONS FOR TREATING PAIN AND INFLAMMATION

[75] Inventors: Shigeho Inaba, Takarazuka; Michihiro Yamamoto, Toyonaka; Kikuo Ishizumi, Ikeda; Kazuo Mori, Kobe; Masao Koshiba, Takarazuka; Hisao Yamamoto, Nishinomiya, all of Japan

[73] Assignee: Sumitomo Chemical Company, Limited, Osaka, Japan

[22] Filed: Oct. 25, 1974

[21] Appl. No.: 518,070

Related U.S. Application Data

[60] Division of Ser. No. 304,357, Nov. 7, 1972, Pat. No. 3,859,237, which is a continuation-in-part of Ser. No. 134,847, April 16, 1971, abandoned.

[30] Foreign Application Priority Data

| Apr. 20, 1970 | Japan | 45-34057 |
| June 3, 1970 | Japan | 45-48570 |
| Oct. 2, 1970 | Japan | 45-86774 |

[52] U.S. Cl. .................................. 424/251
[51] Int. Cl.² .......................... A61K 31/505
[58] Field of Search ....................... 424/251

[56] References Cited
UNITED STATES PATENTS

| 3,549,635 | 12/1970 | Ott | 260/251 |
| 3,551,427 | 12/1970 | Ott | 260/251 |

FOREIGN PATENTS OR APPLICATIONS

| 1,520,743 | 4/1968 | France |

*Primary Examiner*—Stanley J. Friedman
*Attorney, Agent, or Firm*—Stevens, Davis, Miller & Mosher

[57] ABSTRACT

Quinazoline derivatives represented by the formula

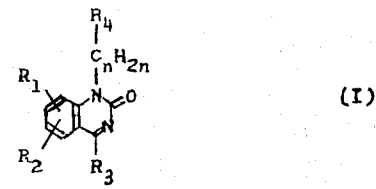

wherein $R_1$ and $R_2$ are individually a hydrogen atom, a halogen atom, a lower alkyl group, a lower alkoxy group, a nitro group, a lower alkylthio group or a lower alkylsulfonyl group; $R_3$ is a hydrogen atom, a lower alkyl group, a lower cycloalkyl group, a napthyl group, a furyl group or a thienyl group; $R_4$ is a lower cycloalkyl group or a trihalomethyl group; and $n$ is an integer of 1 to 3, are novel compounds and have excellent pharmacological properties, particularly as anti-inflammatory and analgesic effects with low toxicity. They can be prepared by treating with ammonia a trihaloacetamidophenylketone derivative of the formula,

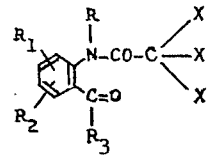

wherein $R_1$, $R_2$ and $R_3$ are as defined above; R is a hydrogen atom or a group of the formula $-C_nH_{2n}-R_4$; and X is a halogen atom.

34 Claims, No Drawings

QUINAZOLINE DERIVATIVES IN PHARMACEUTICAL COMPOSITIONS FOR TREATING PAIN AND INFLAMMATION

CROSS REFERENCE TO THE RELATED APPLICATION

This application is a division of application Ser. No. 304,357, filed Nov. 7, 1972, now U.S. Pat. No. 3,859,237, which is a continuation-in-part of application Ser. No. 134,847, filed Apr. 16, 1971, now abandoned.

This invention relates to novel quinazoline derivatives and a process for the production thereof.

More particularly, the invention pertains to novel quinazoline derivatives represented by the formula,

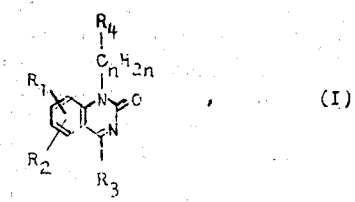

(I)

wherein $R_1$ and $R_2$ are individually a hydrogen atom, a halogen atom, a lower alkyl group, a lower alkoxy group, a nitro group, a lower alkylthio group or a lower alkyl-sulfonyl group; $R_3$ is a hydrogen atom, a lower alkyl group, a lower cycloalkyl group, a naphthyl group, a furyl group or a thienyl group; $R_4$ is a lower cycloalkyl group or a trihalomethyl group; and $n$ is an integer of 1 to 3.

In the compounds represented by the aforesaid formula (I), the term "alkyl" means both straight and branched chain aliphatic hydrocarbon radicals, and the lower alkyl group includes, for example, methyl, ethyl, n-propyl, isopropyl, n-butyl, isobutyl and tertiary-butyl groups; the lower alkoxy group includes, for example, methoxy, ethoxy, n-propoxy, isopropoxy, n-butoxy and tertiary-butoxy groups; the cycloalkyl group includes, for example, cyclopropyl, cyclobutyl, cyclopentyl, cyclohexyl, methyl cyclopropyl, dimethyl cyclopropyl and methyl cyclohexyl groups; and the trihalomethyl group includes, for example, trifluoromethyl, trichloroethyl, chloro-difluoromethyl and bromo-difluoromethyl groups. The alkylene group represented by $C_nH_{2n}$ is a straight chain or branched chain alkylene group having 1 to 3 carbon atoms, and includes, for example, methylene, ethylene, 1-methylethylene, 2-methylethylene and trimethylene groups.

The quinazoline derivatives of the formula (I) have excellent pharmacological properties, particularly as anti-inflammatory and analgesic effects. Illustratively, 1-cyclopropylmethyl-4-(2'-thienyl)-6-chloro-2(1H)-quinaolinone and 1-cyclopropylmethyl-4-(2'-thienyl)-6-methoxy-2(1H)-quinazolinone show remarkable inhibitory action for carrageenin-induced edema in rat, while no toxic symptoms are observed and occult bleeding is negative in feces after oral administration of 1,000 mg/kg in rat. That is, the former inhibits the edeme by 58.6% at the dosage of 200 mg/kg (per os) and 66.0% at 400 mg/kg (per os), and the latter inhibits the edema by 59.8% at 200 mg/kg (per os) and 71.2% at 400 mg/kg (per os).

The compounds of the present invention can be administered orally or parenterally in therapeutic dosage forms with dosage adjusted to individual needs, that is, in solid or liquid dosage forms such as tablet, dragees, capsules, suspensions, solutions, elixirs and the like.

Thus, one object of the present invention is to provide novel quinazoline derivatives excellent in antiinflammatoy effects.

Another object of the present invention is to provide a process for producing such valuable quinazoline derivatives.

Other objects of the present invention will be apparent from the following description In order to accomplish these objects, the present invention provides a process for producing quinazoline derivatives of the aforesaid formula (I), which comprises treating a trihaloacetamidophenylketone derivative represented by the formula,

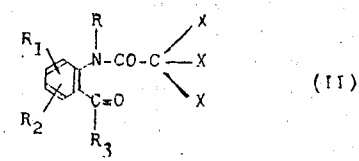

(II)

wherein R is a hydrogen atom or a group of the formula $-C_nH_{2n}-R_4$; $R_1$, $R_2$, $R_3$, $R_4$ and $n$ are as defined above; and X is a halogen atom, with ammonia.

The reaction may be carried out in the presence of a solvent. Examples of the solvent include methanol, ethanol, isopropanol, tertiary-butanol, 2-ethoxyethanol, chloroform, dichloroethane, tetrahydrofuran, dioxane, acetone, pyridine, benzene, toluene, dimethylsulfoxide and dimethylformamide and a mixture thereof. The ammonia is added to the reaction mixture as gaseous ammonia, alcoholic ammonia such as methanolic or ethanolic ammonia, liquid ammonia or ammonium salt (e.g. ammonium acetate, ammonium formate, ammonium carbamate, ammonium carbonate or ammonium phosphate) which is generating ammonia during the reaction. In case the ammonium salt is used, the reaction may be effected in the presence or absence of a base such as, sodium hydroxide, potassium hydroxide, potasssium carbonate, sodium methylate, sodium ethylate, potassium ethylate, triethylamine or pyridine. The reaction generally proceeds at room temperature, but the temperature may be higher or lower, if necessary, to effect the desired control of the reaction.

When R is a hydrogen atom in the formula (II), there are obtained 1-unsubstituted 2(1 H)quinazolinone derivatives represented by the formula,

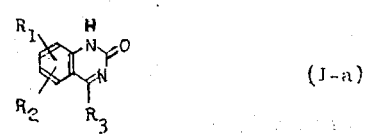

(I-a)

wherein $R_1$, $R_2$ and $R_3$ are as defined above.

They can be further converted to the quinazoline derivatives of the formula (I) by contacting them with a reactive ester of a compound represented by the formula, $$R_4 - C_nH_{2n} - OH \qquad (V)$$

wherein $R_4$ and $n$ are as defined above. Examples of reactive esters include hydrohalic acid esters such as the chlorides, bromides and iodides and sulfonic acid esters such as p-toluenesulfonate, methanesulfonate and trichloromethanesulfonate.

The reaction may be carried out by reacting a compound of the formula (I-a) with a reactive ester of the compound of the formula (V) in the presence of an alkaline agent, or by contacting the compound of the formula (I-a) with an alkaline agent to form the metal salt and then contacting the resulting metal salt with a reactive ester of the compound of the formula (V).

Examples of the alkaline agents include alkali metal hydride such as sodium hydride or potassium hydride, alkali metal amide such as sodium amide or potassium amide, organolithium compound such as butyl lithium or phenyl lithium, alkali metal alkoxide such as sodium methoxide, potassium methoxide, sodium ethoxide, potassium ethoxide or potassium tertiary-butoxide and the like.

The reaction may generally be effected in an organic solvent or solvent mixture.

Suitable solvents include benzene, toluene, xylene, monochlorobenzene, dimethylacetamide, diethylacetamide, dimethylformamide, dioxane and dimethylsulfoxide.

The reaction may be carried out at a temperature within the range between about room temperature and the boiling point of the solvent employed.

The reaction is often accompanied by formation of the quinazoline derivative of the formula (VI),

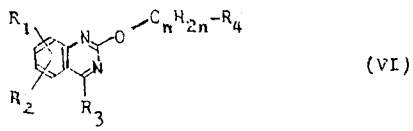

(VI)

wherein $R_1$, $R_2$, $R_3$, $R_4$ and $n$ are as defined above. The separation of the desired quinazoline derivative of the formula (I) from the quinazoline derivative of the formula (VI) may be effected in a conventional manner, illustratively by chromatography.

The trihaloacetamidophenylketone derivatives of the aforesaid formula (II), which are employed in the present invention, are novel compounds unknown in the prior art literature and are quite useful as starting materials. They can be easily prepared by reacting a 2-aminophenylketone derivative represented by the formula,

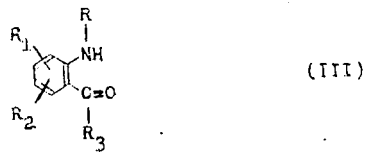

(III)

wherein $R_1$, $R_2$, $R_3$ and R are as defined above, with a trihaloacetic acid, or a reactive derivative thereof, represented by the formula,

(IV)

wherein X is as defined above. Examples of the reactive derivative of the trihaloacetic acid include, for example, acid halides, esters and acid anhydrides. In practicing this process, the use of acid halides such as acid chlorides, acid bromides, is preferable. The reaction may be carried out in the presence or absence of a solvent with or without a condensing agent. The choice of the solvent depends on the trihaloacetic acid or its reactive derivative employed. Thus, the solvent which is inert to the two starting materials can be employed. The suitable solvent is selected from the group consisting of methanol, ethanol, ether, isopropyl ether, tetrahydrofuran, toluene, xylene, chlorobenzene, chloroform, methylene chloride, dichloroethane and the like. In case the reactive derivative of trihaloacetic acid or the condensing agent used is a liquid, the reaction may be carried out in the absence of the solvent. In case an acid halide is used as the reactive derivative, it is advantageous to carried out the reaction in the presence of a basic condensing agent. The condensing agent includes an inorganic base such as, sodium hydroxide, potassium hydroxide, sodium carbonate or potassium carbonate or an organic base such as pyridine, triethylamine or the like. Excess of the aforesaid aminophenylketone derivative of the formula (III) may also be used as the condensing agent. In case a free trihaloacetic acid is used, the suitable condensing agent are, for example, dicyclohexylcarbodiimide, N-cyclohexyl-N'-morpholinoethylcarbodiimide, phosphorus oxychloride, phosphorus trichloride or phosphorus pentachloride.

According to the above process, there are obtained, for example, the following quinazoline derivatives;

1-Cyclopropylmethyl-6-chloro-2(1H)-quinazolinone
1-Cyclopropylmethyl-6-nitro-2(1H)-quinazolinone
1-Cyclopropylmethyl-6-methoxy-2(1H)-quinazolinone
1-Cyclopropylmethyl-4-methyl-2(1H)-quinazolinone
1-Cyclopropylmethyl-4-methyl-6-chloro-2(1H)-quinazolinone
1-Cyclopropylmethyl-4-methyl-6-nitro-2(1H)-quinazolinone
1-Cyclopropylmethyl-4-(n-propyl)-2(1H)-quinazolinone
1-Cyclopropylmethyl-4-isopropyl-2(1H)-quinazolinone
1-Cyclopropylmethyl-4-isopropyl-6-nitro-2(1H)-quinazolinone
1-Cyclohexylmethyl-4-isopropyl-6-nitro-2(1H)-quinazolinone
1-Cyclopropylmethyl-4-cyclohexyl-2(1H)-quinazolinone
1-Cyclopropylmethyl-4-cyclohexyl-6-chloro-2(1H)-quinazolinone
1-Cyclopropylmethyl-4-cyclohexyl-6-nitro-2(1H)-quinazolinone
1-Cyclopropylmethyl-4-cyclohexyl-6-methoxy-2(1H)-quinazolinone
1-Cyclopropylmethyl-4-cyclohexyl-7-nitro-2(1H)-quinazolinone
1-Cyclohexylmethyl-4-cyclohexyl-6-nitro-2(1H)-quinazolinone
1-Cyclopentylmethyl-4-cyclohexyl-6-nitro-2(1H)-quinazolinone
1-Cyclopropylmethyl4-(1'-naphthyl)-2(1H)-quinazolinone
1-Cyclopropylmethyl-4-(1'-naphthyl)-7-methyl-2(1H)-quinazolinone
1-Cyclopropylmethyl-4-(1'-naphthyl)-6-methoxy-2(1H)-quinazolinone 1-Cyclopropylmethyl-4-(2'-naphthyl)-6-methoxy-2(1H)-quinazolinone
1-Cyclopropylmethyl-4-(1'-naphthyl)-6-methylthio-2(1H)-quinazolinone
1-Cyclopropylmethyl-4-(1'-naphthyl)-6-methylsulfonyl-2(1H)-quinazolinone
1-Cyclohexylmethyl-4-(1'-naphthyl)-6-nitro-2(1H)-quinazolinone
1-Cyclopropylmethyl-4-(2'-furyl)-2(1H)-quinazolinone
1-Cyclopropylmethyl-4-(2'-furyl)-6-chloro-2(1H)-quinazolinone
1-Cyclopropylmethyl-4-(2'-furyl)-6-methyl-2(1H)-quinazolinone
1-Cyclopropylmethyl-4-(2'-furyl)-7-methyl-2(1H)-quinazolinone
1-Cyclopropylmethyl-4-(2'-furyl)-6-methoxy-2(1H)-quinazolinone
1-Cyclopropylmethyl-4-(2'-furyl)-6-nitro-2(1H)-quinazolinone
1-Cyclopropylmethyl-4-(2'-furyl)-6-methylthio-2(1H)-quinazolinone
1-Cyclopropylmethyl-4-(2'-furyl)-6-methylsulfonyl-2(1H)-quinazolinone
1-Cyclohexylmethyl-4-(2'-furyl)-6-nitro-2(1H)-quinazolinone
1-Cyclopropylmethyl-4-(2'-thienyl)-2(1H)-quinazolinone
1-Cyclopropylmethyl-4-(2'-thienyl)-6-chloro-2(1H)-quinazolinone
1-Cyclopropylmethyl-4-(2'-thienyl)-6-methyl-2(1H)-quinazolinone
1-Cyclopropylmethyl-4-(2'-thienyl)-7-methyl-2(1H)-quinazolinone
1-Cyclopropylmethyl-4-(2'-thienyl)-6,7-dimethyl-2(1H)-quinazolinone
1-Cyclopropylmethyl-4-(2'-thienyl)-6-methoxy-2(1H)-quinazolinone
1-Cyclopropylmethyl-4-(2'-thienyl)-8-methoxy-2(1H)-quinazoline
1-Cyclopropylmethyl-4-(2'-thienyl)-6-methoxy-8-methyl-2(1H)-quinazolinone
1-Cyclopropylmethyl-4-(2'-thienyl)-6-nitro-2(1H)-quinazolinone
1-Cyclopropylmethyl-4-(2'-thienyl)-6-methylthio-2(1H)-quinazolinone
1-Cyclopropylmethyl-4-(2'-thienyl)-6-methylsulfonyl-2(1H)-quinazolinone
1-(2'-Cyclopropylethyl)-4-(2'-thienyl)-6-nitro-2(1H)-quinazolinone
1-Cyclohexylmethyl-4-(2'-thienyl)-6-nitro-2(1H)-quinazolinone
1-(2', 2', 2'-Trifluoroethyl)-2(1H)-quinazolinone
1-(2', 2', 2'-Trifluoroethyl)-4-methyl-6-nitro-2(1H)-quinazolinone
1-(2', 2', 2'-Trifluoroethyl)-4-isopropyl-6-methoxy-2(1H)-quinazolinone
1-(2', 2', 2'-Trifluoroethyl)-4-cyclohexyl-2(1H)-quinazolinone
1-(2', 2', 2'-Trifluoroethyl)-4-cyclohexyl-6-chloro-2(1H)-quinazolinone
1-(2', 2', 2'-Trifluoroethyl)-4-cyclohexyl-6-methoxy-2(1H)-quinazolinone
1-(2', 2', 2'-Trifluoroethyl)-4-cyclohexyl-6-nitro-2(1H)-quinazolinone
1-(2',2', 2'-Trifluoroethyl)-4-(1'-naphthyl)-6-methoxy-2(1H)-quinazolinone
1-(2', 2',2'-Trifluoroethyl)-4-(2'-furyl)-2(1H)-quinazolinone
1-(2', 2', 2'-Trifluoroethyl)-4-(2'-furyl)-6-chloro-2(1H)-quinazolinone
1-(2', 2', 2'-Trifluoroethyl)-4-(2'-furyl)-6-methoxy-2(1H)-quinazolinone
1-(2', 2', 2'-Trifluoroethyl)-4-(2'-furyl)-6-nitro-2(1H)-quinazolinone
1-(2', 2', 2'-Trifluoroethyl)-4-(2'-thienyl)-2(1H)-quinazolinone
1-(2', 2',2'-Trifluoroethyl)-4-(2'-thienyl)-6-chloro-2(1H)-quinazolinone
1-(2', 2', 2'-Trifluoroethyl)-4-(2'-thienyl)-6-methyl-2(1H)-quinazolinone
1-(2',2',2'-Trifluoroethyl)-4-(2'-thienyl)-7-methyl-2(1H)-quinazolinone
1-(2',2',2'-Trifluoroethyl)-4-(2'-thienyl)-8-methyl-2(1H)-quinazolinone
1-(2',2',2'-Trifluoroethyl)-4-(2'-thienyl)-6-methoxy-2(1H)-quinazolinone
1-(2',2',2'-Trifluoroethyl)-4-(2'-thienyl)-6,7-dimethoxy-2(1H)-quinazolinone
1-(2',2',2'-Trifluoroethyl)-4-(2'-thienyl)-6-nitro-2(1H)-quinazolinone
1-(2',2',2'-Trifluoroethyl)-4-(2'-thienyl)-6-methylthio-2(1H)-quinazolinone
1-(2',2',2'-Trifluoroethyl)-4-(2'-thienyl)-6-methylsulfonyl-2(1H)-quinazolinone
1-(2',2',2'-Trichloroethyl)-4-(2'-thienyl)-2(1H)-quinazolinone
1-(2',2',2'-Trichloroethyl)-4-(2'-thienyl)-6-methoxy-2(1H)-quinazolinone
1-(2',2',2'-Trichloroethyl)-4-(2'-thienyl)-6-nitro-2(1H)-quinazolinone
1-(2'-Chloro-2',2'-difluoroethyl)-4-(2'-thienyl)-2(1H-quinazolinone.

This invention is further disclosed in the following Examples of more preferred embodiments thereof, which are presented for the purpose of illustration and it is not intended to limit the scope of the invention.

EXAMPLE 1

To a solution of 2.74 g of 4-(2'-thienyl)-2(1H)-quinazolinone in 60 ml of dimethylformamide was added portionwise 0.50 g of 63% sodium hydride. The mixture was heated at 55°–60°C for 30 minutes with stirring, and cooled to room temperature. Thereafter, to the mixture was added 3.6 g of 90% cyclopropylmethyl bromide and the resulting mixture was further heated and stirred at 100°C for 6 hours. After cooling, the reaction mixture was poured into 300 ml of water and extracted twice with chloroform. The chloroform extracts were combined, washed with water and dried over anhydrous sodium sulfate. Then the solvent was removed under reduced pressure to give oily brown residue, which was chromatographed on silica gel using chloroform as an eluent. Thereby, there were obtained 2.0 g of 1-cyclopropylmethyl-4-(2'-thienyl)-2(1H)-quinazolinone and 1.0 g of 2-cyclopropylmethoxy-4-(2'-thienyl)quinazoline. The former was recrystallized from a mixture of ethanol and isopropyl ether to give light yellow needles, m.p. 89.0°–91.0°C. The latter was recrystallized from the mixture of ethanol and petroleum benzine to give light yellow fine crystals, m.p. 83.0°–84.0°C.

4-(2'-Thienyl)-2(1H)-quinazolinone used as the starting material was prepared as follows:

To a solution of 5.08 g of 2-aminophenyl 2'-thienyl ketone and 2.5 g of triethylamine in 50 ml of ether was added dropwise with ice-cooling 4.55 g of trichloroacetyl chloride. After the mixture was stirred at room temperature for 2 hours, the ether layer was washed with water and dried over anhydrous sodium sulfate. Then the solvent was removed under reduced pressure to give oily brown residue. The residue was crystallized from ethanol to obtain 7.59 g of 2-trichloroacetamidophenyl 2'-thienyl ketone as yellow prisms, m.p. 101.5°–103.5°C.

To a solution of 5.23 g of 2-trichloroacetamidophenyl 2'-thienyl ketone in 50 ml of dimethyl sulfoxide was added 2.31 g of ammonium acetate. The mixture was heated in a oil bath at 100°C for 3 hours. After cooling, the mixture was poured into 300 ml of water, and resulting precipitate was collected by filtration, washed with water and dried to obtain 3.22 g of 4-(2'-thienyl)-2(1H)-quinazolinone, which was recrystallized from a mixture of chloroform and dimethylformamide to give light yellow prisms, m.p. 254.5° –256.0°C.

EXAMPLE 2

Using a procedure similar to that described in Example 1, but replacing 4-(2'-thienyl)-2(1H)-quinazolinone by 2.96 g of 4-(2'-furyl)-6-chloro-2(1H)-quinazolinone, there was obtained 1.4 g of 1-cyclopropylmethyl-4-(2'-furyl)-6-chloro-2(1H)-quinazolinone and 1.3 g of 2-cyclopropylmethoxy-4-(2'-furyl)-6-chloroquinazoline. The former was recrystallized from a mixture of ethanol and isopropyl ether to give yellow prisms, m.p. 160.0°–161.0°C. The latter was recrystallized from isopropyl ether to give yellow needles, m.p. 109.0°–110.0°C.

4-(2'-Furyl)-6-chloro-2(1H)-quinazolinone used as the starting material was prepared as follows:

To a solution of 8.86 g of 2-amino-5-chlorophenyl 2'-furyl ketone and 4.0 g of triethylamine in the mixture of 100 ml of ether and 40 ml of chloroform was added dropwise ice-cooling 7.3 g of trichloroacetyl chloride. The mixture was stirred at room temperature for 2 hours. Then the organic layer was washed with water and dried over sodium sulfate, and the solvent was removed under reduced pressure. The residue was chromatographed on silica gel using benzene as an eluent to obtain 10.7 g of 2-trichloroacetamido-5-chlorophenyl 2'-furyl ketone, which was recrystallized from a mixture of ethanol and petroleum benzine to give yellow crystals, m.p. 80.0°–81.0°C.

To a solution of 5.51 g of 2-trichloroacetamido-5-chlorophenyl2'-furyl ketone in 50 ml of dimethyl sulfoxide was added 2.31 g of ammonium acetate. The mixture was heated in an oil bath at 95°C for 1 hour. After cooling, the mixture was poured into 300 ml of water, and resulting precipitate was collected by filtration, washed with water and ether in order and then dried to obtain 3.25 g of 4-(2'-furyl)-6-chloro-2(1H)-quinazolinone, which was recrystallized from dimethylformamide to give brown needles, m.p. >300°C.

EXAMPLE 3

Using a procedure similar to that described in Example 1, but replacing 4-(2'-thienyl)-2(1H)-quinazolinone by 3.15 g of 4(2'-thienyl)-6-chloro-2(1H)-quinazolinone, there were obtained 2.05 g of 1-cyclopropylmethyl-4-(2'-thienyl)-6-chloro-2(1H)-quinazolinone which was recrystallized from a mixture of ethanol, ether and petroleum benzine to give yellow prisms, m.p. 14.0°– 141.0°C, and 1.65 g of 2-cyclopropylmethoxy-4-(2'-thienyl)-6-chloroquinazoline which was recrystallized from a mixture of ethanol and petroleum benzine to give light yellow needles, m.p. 97.0° – 98.0°C.

4-(2'-Thienyl)-6-chloro-2(1H)-quinazolinone used as the starting material was also prepared by the procedure similar to that described in Example 1, but replacing 2-aminophenyl 2'-thienyl ketone by 2-amino-5-chlorophenyl 2'-thienyl ketone. Accordingly, there were obtained 2-trichloroacetamido-5-chlorophenyl 2'-thienyl ketone, m.p. 97.0° – 98.0°C and subsequently 4-(2'-thienyl)-6-chloro-2(1H)-quinazolinone, m.p. > 300°C.

EXAMPLE 4

To a solution of 3.94 g of 4-(2'-thienyl)-6 -chloro-2(1H)-quinazolinone in 150 ml of dimethylformamide was added portionwise 0.65 g of 63% sodium hydride. The mixture was heated at 55°C for 1 hour with stirring. Thereafter, to the mixtue was added 6.3 g of 2,2,2-trifluoroethyl iodide and the resulting mixture was further heated at 135°C for 7 hours. After cooling, the reaction mixture was poured into 800 ml of water and the precipitate was collected by filtration, washed with water and dried. The crude product was chromatographed on silica gel using chloroform as an eluent. Thereby, there were obtained 2.80 g of 1-(2',2',2'-trifluoroethyl)-4-(2'-thienyl)-6-chloro-2(1H)-quinazolinone and 2.07 g of 2-(2',2',2'-trifluoroethoxy)-4-(2'-thienyl)-6-chloroquinazoline.

The former was recrystallized from chloroform to give light yellow fine needles, m.p. 266.0° – 227.0°C. The latter was recrystallized from ethanol to give light yellow needles, m.p. 107.0° –108.0°C.

EXAMPLE 5

Using a procedure similar to that described in Example 1, but replacing 4-(2'-thienyl)-2(1H)-quinazolinone by 4-methyl-6-chloro-2(1H)-quinazolinone, there were obtained 1-cyclopropylmethyl-4-methyl-6-chloro-2(1H)-quinazolinone as brownish yellow needles, m.p. 164° –165°C and 2-cyclopropylmethoxy-4-methyl-6-chloroquinazoline as an orange oil.

4-Methyl-6-chloro-2(1H)-quinazolinone used as the starting material was prepared as follows:

To a solution of 6.78 g of 2-amino-5-chloroacetophenone and 4.0 g of triethylamine in 100 ml of ether was added dropwise with ice-cooling 7.3 g of trichloroacetyl chloride. After the mixture was stirred at room temperature for 2 hours, the ether layer was washed with water and dried over anhydrous sodium sulfate. And then, the solvent was removed under reduced pressure to give oily brown residue, which was crystalized from the mixture of ethanol and petroleum benzine to obtain 9.92 g of 2-trichloroacetamido-5-chloroacetophenone as light yellow needles, m.p. 85.0° – 87.0°C.

To a solution of 4.73 g of 2-trichloroacetamido-5-chloroacetophenone in 50 ml of dimethyl sulfoxide was added 2.31 g of ammonium acetate. The mixture was heated in an oil bath at 100° – 105°C for 2 hours. After cooling, the mixture was poured into 300 ml of water, and the resulting precipitate was collected by filtration, washed with water and dried to give 2.78 g of 4-methyl-6-chloro-2(1H)-quinazolinone which was recrystallized from dimethyl sulfoxide to give brownish yellow powder. m.p. > 270°C.

EXAMPLE 6

Using a procedure similar to that described in Example 1, but replacing 4-(2'-thienyl)-2(1H)-quinazolinone by 3.94 g of 4-cyclohexyl-6-chloro-2(1H)-quinazolinone, there were obtained 1.91 g. of 1-cyclopropylmethyl-4-cyclohexyl-6-2(1H)-quinazolinone and 1.62 g of 2-cyclopropylmethoxy-4-cyclohexyl-6-chloroquinazoline.

The former was recrystallized from ethanol to give colorless needles, m.p. 157° –157.5°C. The latter was recrystallized from isopropyl ether to give colorless needles, m.p. 108.5° – 109.0°C.

4-Cyclohexyl-6-chloro-2(1H)-quinazolinone used as the starting material was prepared as follows:

To a solution of 14.3 g of 2-amino-5-chlorophenyl cyclohexyl ketone and 6.0 g of triethylamine in the mixture of 100 ml of ether and 30 ml of methylene chloride was added dropwise with ice-cooling 11.0 g of trichloroacetyl chloride. After the mixture was stirred at room temperature for 2 hours, the organic layer was washed with water and dried over anhydrous sodium sulfate. Then the solvent was removed under reduced pressure to give oily residue. The residue was crystallized from ether to obtain 18.5 g of 2-trichloroacetamido-5-chlorophenyl cyclohexyl ketone as light yellow crystals, m.p. 93.0°–93.5°C.

To a solution of 7.66 g of 2-trichloroacetamido-5-chlorophenyl cyclohexyl ketone in 150 ml of dimethyl sulfoxide was added 4.0 g of triethylamine and 7.71 g of ammonium acetate. The mixture was left at room temperature for 1 day, and poured into 700 ml of water. The resulting precipitate was collected by filtration, washed with water and dried to obtain 5.29 g of 4-cyclohexyl-6-chloro-2(1H)-quinazolinone, which was recrystallized from chloroform to give colorless needles, m.p. 269.5°–270.5°C.

EXAMPLE 7

Using a procedure similar to that described in Example 6, there were obtained 1-cyclopropylmethyl-4-cyclohexyl-6-nitro-2(1H)-quinazolinone as light brown needles, m.p. 110.0° – 111.5°C and 2-cyclopropylmethoxy-4-cyclohexyl-6-nitroquinazoline as colorless needles, m.p. 147.0° – 148.0°C.

EXAMPLE 8

Using a procedure smilar to that described in Example 4, but replacing 4-(2'-thienyl)-6-chloro-2(1H)-quinazolinone by 4-cyclohexyl-6-chloro-2(1H)-quinazolinone, there were obtained 1-(2',2',2'-trifluoroethyl)-4-cyclohexyl-6-chloro-2(1H)-quinazolinone, m.p. 181.0°–181.5°C. and 2-(2',2',2'-trifluoroethoxy)-4-cyclohexyl-6-chloroquinazoline, m.p. 113.0°–114.0°C.

EXAMPLE 9

To a solution of 2.92 g of 2-cyclopropylmethylamino-5-chlorophenyl 2'-thienyl ketone and 1.82 g of trichloroacetyl chloride in 50 ml of ether was added dropwise with ice-cooling 1.0 g of triethylamine. The mixture was stirred at room temperature for 1 hour and then refluxed for 2 hours. After cooling, the reaction mixture was washed with water and dried over anhydrous sodium sulfate. Then the solvent was removed to give 4.3 g of 2(N-cyclopropylmethyl-trichloroacetamido)-5-chlorophenyl 2'-thienyl ketone as an brown oil.

The crude 2-(N-cyclopropylmethyl-trichloroacetamido)-5-chlorophenyl 2'-thienyl ketone thus obtained was dissolved in 50 ml of ethanol. To the solution was added 5 g of ammonium acetate. The mixture was refluxed with stirring for 10 hours and then concentrated. After cooling with ice, the precipitate was collected by filtration, washed successively with ether and water, and dried to give 1-cyclopropylmethyl-4-(2'-thienyl)-6-chloro-2(1H)-quinazolinone, which was recrystallized from ethanol to give yellow needles, m.p. 134.5° – 135.5°C.

EXAMPLE 10

Using a procedure similar to that described in Example 9, there were produced the following compounds.

1-Cyclopropylmethyl-4-methyl-6-chloro-2(1H)-quinazolinone, m.p. 164° – 165°C.
1-Cyclopropylmethyl-4-(1'-naphthyl)-6-methoxy-2(1H)-quinazolinone, m.p. 110°C.
1-Cyclopropylmethyl-4-(2'-thienyl)-6-methoxy-2(1H)-quinazolinone, m.p. 146° – 146.5°C.
1-Cyclopropylmethyl-4-(2'-thienyl)-7-methyl-2(1H)-quinazolinone, m.p. 149.0° – 150.0°C.
1-Cyclopropylmethyl-4-(2°-thienyl)-6-methylthio-2(1H)-quinazolinone, m.p. 108.0°– 108.5°C.
1-Cyclopropylmethyl-4-(2'-thienyl)-6-methylsulfonyl-2(1H)-quinazolinone, m.p. 130°C (decomp).
1-(2',2',2'-Trifluoroethyl)-4-(2'-thienyl)-6-chloro-2(1H)-quinazolinone, m.p. 226.0° –227.0°C.

What is claimed is:

1. A pharmaceutical composition containing a pharmaceutically acceptable carrier and as an active ingredient an anti-inflammatorily and analgesically effective amount of a quinazoline derivative represented by the formula,

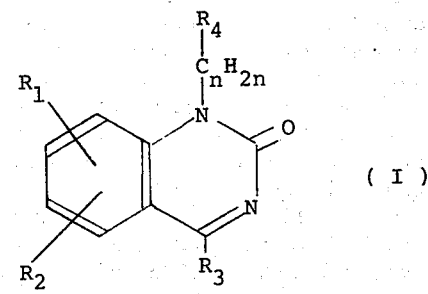

( I )

wherein $R_1$ and $R_2$ are individually hydrogen, halogen, methyl, ethyl, n-propyl, isopropyl, n-butyl, isobutyl, methoxy, ethoxy, n-propoxy, isopropoxy, n-butoxy, nitro, methylthio, ethylthio, n-propylthio, isopropylthio, n-butylthio, isobutylthio, methylsulfonyl, ethylsulfonyl, n-propylsulfonyl, isopropylsulfonyl, n-butylsulfonyl, or isobutylsulfonyl; $R_3$ is hydrogen, $C_{1-4}$ alkyl, cyclo-$C_{3-6}$ alkyl, napthyl, furyl, or thienyl; $R_4$ is cyclo-$C_{3-6}$ aklyl or trihalomethyl; and $n$ is an integer of 1 to 3.

2. A pharmaceutical composition according to claim 1, wherein $R_4$ of said quinazoline derivative is $C_{3-6}$ cycloalkyl.

3. A pharmaceutical composition according to claim 1, wherein $R_3$ of said quinazoline derivative is thienyl, $R_4$ is cyclopropyl and $n$ is 1.

4. A pharmaceutical composition according to claim 1, wherein $R_4$ is trihalomethyl and $R_3$ is thienyl or cyclo-$C_{3-6}$ alkyl.

5. A pharmaceutical composition according to claim 1, wherein said quinazoline derivative is 1-cyclopropyl-methyl-4-(2'-thienyl)-2(1H)-quinazolinone.

6. A pharmaceutical composition according to claim 1, wherein said quinazoline derivative is 1-cyclopropyl-methyl-4-(2'-thienyl)-6-chloro-2(1H)-quinazolinone.

7. A pharmaceutical composition according to claim 1, wherein said quinazoline derivative is 1-cyclopropyl-methyl-4-(2'-thienyl)-6-methyl-2(1H)-quinazolinone.

8. A pharmaceutical composition according to claim 1, wherein said quinazoline derivative is 1-cyclopropyl-methyl-4-(2'-thienyl)-7-methyl-2(1H)-quinazolinone.

9. A pharmaceutical composition according to claim 1, wherein said quinazoline derivative is 1-cyclopropyl-methyl-4-(2'-thienyl)-6,7-dimethyl-2(1H)-quinazolinone.

10. A pharmaceutical composition according to claim 1, wherein said quinazoline derivative is 1-cyclopropylmethyl-4-(2'-thienyl)-6-methoxy-2(1H)-quinazolinone.

11. A pharmaceutical composition according to claim 1, wherein said quinazoline derivative is 1-cyclopropylmethyl-4-(2'-thienyl)-8-methoxy-2(1H)-quinazolinone.

12. A pharmaceutical composition according to claim 1, wherein said quinazoline derivative is 1-cyclopropylmethyl-4-(2'-thienyl)-6-methoxy-8-methyl-2(1H)-quinazolinone.

13. A pharmaceutical composition according to claim 1, wherein said quinazoline derivative is 1-cyclopropylmethyl-4-(2'-thienyl)-6-nitro-2(1H)-quinazolinone.

14. A pharmaceutical composition according to claim 1, wherein said quinazoline derivative is 1-cyclopropylmethyl-4-(2'-thienyl)-6-methylthio-2(1H)-quinazoline.

15. A pharmaceutical composition according to claim 1, wherein said quinazoline derivative is 1-cyclopropylmethyl-4-(2'-thienyl)-6-methyl-sulfonyl-2(1H)-quinazolinone.

16. A pharmaceutical composition according to claim 1, wherein said quinazoline derivative is 1-(2'-cyclopropylethyl)-4-(2'-thienyl)-6-nitro-2(1H)-quinazolinone.

17. A pharmaceutical composition according to claim 1, wherein said quinazoline derivative is 1-cyclohexylmethyl-4-(2'-thienyl)-6-nitro-2(1H)-quinazolinone.

18. A pharmaceutical composition according to claim 1, wherein said quinazoline derivative is 1-(2',2',2'-trifluoroethyl)-4-cyclohexyl-2(1H)-quinazolinone.

19. A pharmaceutical composition according to claim 1, wherein said quinazoline derivative is 1-(2',2',2'-trifluoroethyl)-4-cyclohexyl62(1H)-quinazolinone.

20. A pharmaceutical composition according to claim 1, wherein said quinazoline derivative is 1-(2',2',2'-trifluoroethyl)-4-cyclohexyl-6-nitro-2(1H)-quinazolinone.

21. A pharmaceutical composition according to claim 1, wherein said quinazoline derivative is 1-(2',2',2'-trifluoroethyl)-4-(2'-thienyl)-2(1H)-quinazolinone.

22. A pharmaceutical composition according to claim 1, wherein said quinazoline derivative is 1-(2',2',2',-trifluoroethyl)-4-(2-trienyl)-6-chloro-2(1H)-quinazolinone.

23. A pharmaceutical composition according to claim 1, wherein said quinazoline derivative is 1-(2',2',2'-trifluoroethyl)-4-(2'-thienyl)-6-methyl-2(1H)-quinazolinone.

24. A pharmaceutical composition according to claim 1, wherein said quinazoline derivative is 1-(2',2',2'-trifluoroethyl)-4-(2'-thienyl)-7-methyl-2(1H)-quinazolinone.

25. A pharmaceutical composition according to claim 1, wherein said quinazoline derivative is 1-(2',2',2'-trifluoroethyl)-4-(2'-thienyl)-8-methyl-2(1H)-quinazolinone.

26. A pharmaceutical composition according to claim 1, wherein said quinazoline derivative is 1-(2',2',2'-trifluoroethyl)-4-(2'-thienyl)-6-methoxy-2(1H)-quinazolinone.

27. A pharmaceutical composition according to claim 1, wherein said quinazoline derivative is 1-(2',2',2'-trifluoroethyl)-4-(2'-thienyl)-6,7-dimethoxy-2(1H)-quinazlinone.

28. A pharmaceutical composition according to claim 1, wherein said quinazoline derivative is 1-(2',2',2'-trifluoroethyl)-4-(2'-thienyl)-6-nitro-2(1H)-quinazolinone.

29. A pharmaceutical composition according to claim 1, wherein said quinazoline derivative is 1-(2',2',2'-trifluoroethyl)-4-(2'-thienyl)-6-methylthio-2(1H)-quinazolinone.

30. A pharmaceutical composition according to claim 1, wherein said quinazoline derivative is 1-(2',2',2'-trifluoroethyl)-4-(2'-thienyl)-6-methylsulfonyl-2(1H)-quinazolinone.

31. A pharmaceutical composition according to claim 1, wherein said quinazoline derivative is 1-(2',2',2'-trichloroethyl)-4-(2'-thienyl)-2(1H)-quinazolinone.

32. A pharmaceutical composition according to claim 1, wherein said quinazoline derivative is 1-(2',2',2'-trichloroethyl)-4-(2'-thienyl)-6-methoxy-2(1H)-quinazolinone.

33. A pharmaceutical composition according to claim 1, wherein said quinazoline derivative is 1-(2', 2', 2'-trichloroethyl)-4-(2'-thienyl)-6-nitro-2(1H)-quinazolinone.

34. A pharmaceutical composition according to claim 1, wherein said quinazoline derivative is 1-(2'-chloro-2',2'-difluoroethyl)-4(2'-thienyl)-2(1H)-quinazolinone.

* * * * *